United States Patent

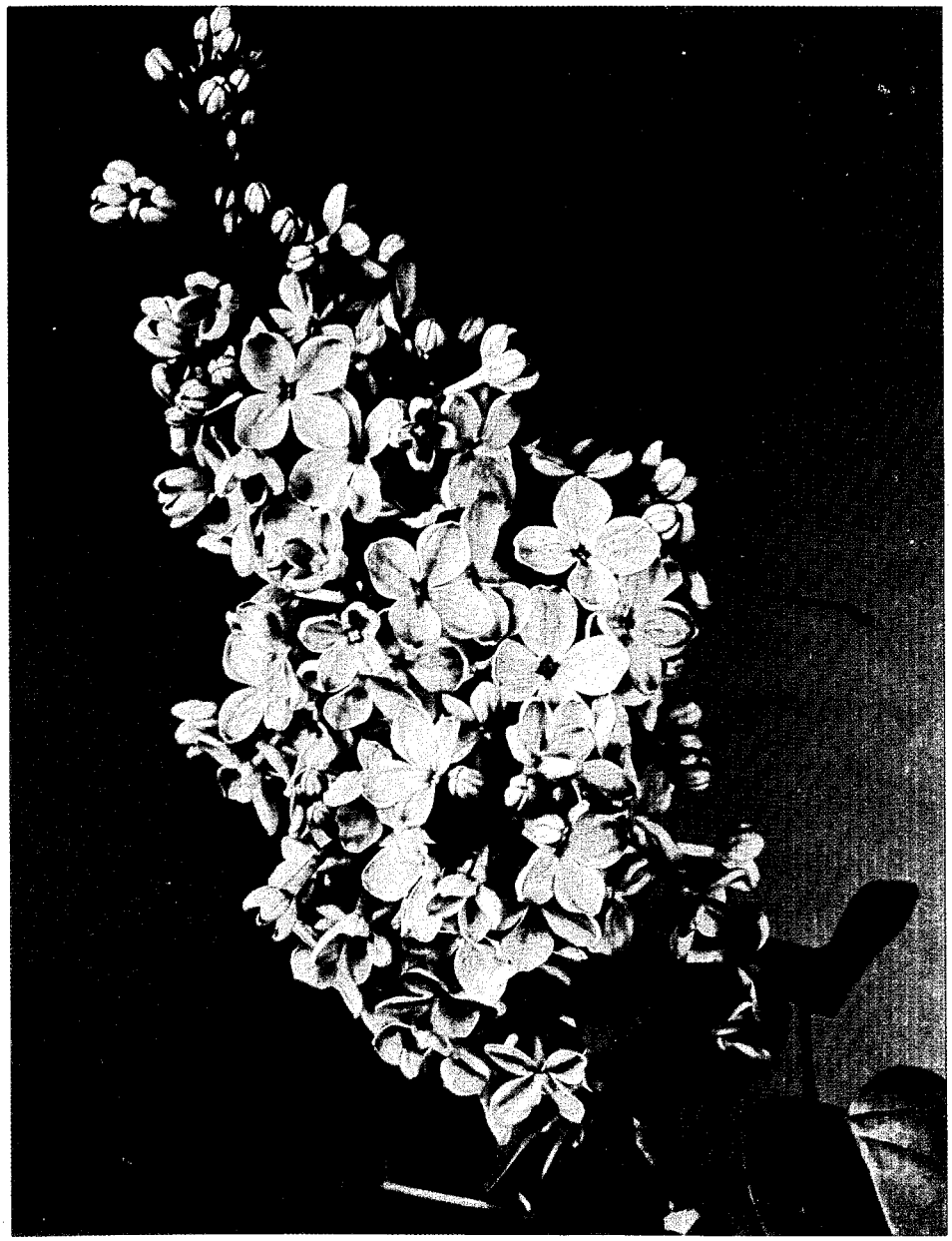

Plant Pat. 3,895

Patented May 25, 1976

3,895

LILAC PLANT

Walter E. Lammerts, Corralitos, Calif., assignor to Hines Wholesale Nurseries, Santa Ana, Calif.

Filed Mar. 24, 1975, Ser. No. 561,326

Int. Cl. A01h *5/00*

U.S. Cl. Plt.—66 1 Claim

The present invention relates to a new and distinct variety of lilac plant originated by me by crossing two unnamed and unpatented seedlings, each of which was derived from seedlings derived from various crosses I have made with seed of an unnamed and unpatented early-leafing variety identified by me in my breeding records by the identification number C112.

The primary objective in making this cross was to further and improve the objectives set forth in Plant Pat. 1,238 previously granted to me on Jan. 5, 1954. As set forth in this prior application, I had produced a lilac which would flower normally in Southern California and comparable climatic areas having short and mild winters. The present invention relates to a lilac plant which requires less than normal winter-chilling required by most lilacs, including the usual eastern lilacs, and still produces normal flowering bloom clusters.

My new variety is characterized by its ability to achieve normal flowering without requiring normal winter-chilling; by its regularity and abundance of bloom consisting of very large flower clusters measuring from 7 to 10 inches in length and from 7 to 12 inches in width; and by the size of relatively large florets, at times measuring from ⅞ of an inch to 13/16 inches in diameter. Occasional flower clusters will be as large as 12 inches in both length and width.

The new variety was asexually reproduced by me on cultivated property known as Descanso Distributors at Chino, Calif. Reproduction of this new variety was made by cuttings and also by budding to Ligustrum understock, and as a result established that the foregoing distinguishing characteristics come true to form and are established and transmitted through succeeding propagations.

The drawing which accompanies this petition shows a typical view of the flowers and foliage of my new lilac variety and is portrayed in color as fairly as can possibly be obtained by this method of illustration.

To facilitate identification of the important colors, I have used the color terminology of the R.H.S. Colour Chart issued by the Royal Horticultural Society of London.

Locality where grown and observed: Descanso Distributors Nursery in Chino, Calif.

Parentage: Seedling resulting from planned propagation.

Seed parent.—A large-petalled unpatened seedling of of an unnamed early-leafing variety identified in my breeding records as C112, crossed to a seedling derived from seed obtained by open pollenation of an unpatented variety, Syringa "Lamertine."

Pollen parent.—A deep pink unnamed seedling derived from seed produced by open pollenation of a seedling of an unpatented variety, S. "Buffon," identified in my breeding records as 42–109–4.

The seeds which were produced by this cross in 1950, were sown in 1951, and plants first bloomed in 1953.

Blooming habit: Early, usually from about the early part of March to mid-April in Southern California. In full flower and leaf by the end of March.

*The plant*

Form of plant: Bush.

Growth: Upright; vigorous, compact.

Branches:

New growth is in Green Group, Plates 143A to 143B.

Mature growth is in the Greyed-Green Group, Plate 197C to Plate 197D.

Foliage:

Size.—From about 2 inches to 2½ inches wide, and from about 2¾ inches to 3½ inches long.

Quantity.—Abundant.

Shape.—Ovate with an acuminate tip, and a cordate base. The leaf margin is entire.

Venation.—Pinnate.

Arrangement.—Opposite.

Color.—New leaves are in the Yellow-Green Group, Plates 46A to 146B.

Mature leaves are in the Green Group, Plates 141B to 141C.

*The flower*

Bud: Individual florets of cluster.

Size.—Large.

Form.—Stubby; tending to be globular-elongate.

Color.—In the Red-Purple Group, Plates 70B to 70C.

Bloom: Individual florets of cluster, about ¾ of an inch, to about 1¼ inches in diameter. Florets are borne in large clusters measuring from 7 to 10 inches in length and from 7 to 12 inches in width, with occasional clusters as large as 12 inches in both length and width. Individual raceme lengths comprising the cluster range from 2 inches to 2½ inches in length.

Color.—In the Violet-Blue Group, Plates 94C to 94D. There are present tints of Red-Purple Group, Plate 70C. The petal colors fade towards the base to Violet-Blue Group, Plates 92B to 92C. Underside of the flower varies from Purple Group, Plate 75B to Plate 75C. The flowers have a distinct pleasing fragrance.

I claim:

1. A new and distinct variety of lilac plant, substantially as herein shown and described, characterized particularly as to novelty by its relatively short and mild winter-chilling requirements, by its regular and abundant production of large flower clusters consisting of large individual florets, by its vigorous habit of plant growth, and by its abundant production of large and attractive foliage.

No references cited.

ROBERT E. BAGWILL, Primary Examiner